(12) United States Patent
Jorritsma

(10) Patent No.: US 7,796,799 B2
(45) Date of Patent: Sep. 14, 2010

(54) INSPECTION DEVICE FOR LOOSE OBJECTS, SUCH AS TABLETS

(75) Inventor: Minne Jorritsma, Amsterdam (NL)

(73) Assignee: HD Medi B.V., Lelystad (NL)

( * ) Notice: Subject to any disclaimer, the term of this patent is extended or adjusted under 35 U.S.C. 154(b) by 259 days.

(21) Appl. No.: 10/544,745

(22) PCT Filed: Mar. 13, 2003

(86) PCT No.: PCT/NL03/00189

§ 371 (c)(1),
(2), (4) Date: Apr. 7, 2006

(87) PCT Pub. No.: WO2004/072626

PCT Pub. Date: Aug. 26, 2004

(65) Prior Publication Data

US 2006/0213816 A1 Sep. 28, 2006

(30) Foreign Application Priority Data

Feb. 14, 2003 (NL) .................................. 1022679

(51) Int. Cl.
*B07C 5/00* (2006.01)
(52) U.S. Cl. ..................................... 382/141; 209/576
(58) Field of Classification Search ................. 209/576; 382/141

See application file for complete search history.

(56) References Cited

U.S. PATENT DOCUMENTS

| | | | |
|---|---|---|---|
| 3,656,274 A * | 4/1972 | Vind ............................ 53/562 |
| 3,871,156 A | 3/1975 | Koenig et al. |
| 3,882,316 A * | 5/1975 | Garris .................... 250/559.15 |
| 3,942,900 A * | 3/1976 | Garris ...................... 356/239.1 |
| 4,236,413 A * | 12/1980 | Schmid et al. ................. 73/821 |
| 4,614,076 A * | 9/1986 | Rathemacher ................ 53/433 |
| 4,691,231 A * | 9/1987 | Fitzmorris et al. ........... 348/127 |
| 5,132,791 A * | 7/1992 | Wertz et al. .................... 348/88 |
| 5,638,417 A * | 6/1997 | Boyer et al. .................... 377/7 |
| 6,116,409 A * | 9/2000 | Yokajty et al. .............. 198/771 |
| 6,324,253 B1 * | 11/2001 | Yuyama et al. ................ 378/57 |
| 6,505,461 B1 * | 1/2003 | Yasunaga ..................... 53/562 |

FOREIGN PATENT DOCUMENTS

| | | |
|---|---|---|
| DE | 101 12 213 | 10/2002 |
| JP | 3-248047 | 11/1991 |
| JP | 7-200820 | 8/1995 |
| JP | 9-113419 | 5/1997 |

* cited by examiner

*Primary Examiner*—Vu Le
*Assistant Examiner*—Michael Vanchy, Jr.
(74) *Attorney, Agent, or Firm*—Oblon, Spivak, McClelland, Maier & Neustadt, L.L.P.

(57) ABSTRACT

An inspection device for loose objects, for example tablets that may or may not be packaged, including a conveying mechanism for conveying the objects to at least one inspection area. The inspection device includes a mechanical impulse mechanism for moving the objects apart prior to or during transport to the at least one inspection area. This leads in particular to an improved automatic verification of the number, the shape, the color and the size of the tablets, as a result of which fewer errors will occur in the eventual administration of medicines to persons, or patients.

19 Claims, 1 Drawing Sheet

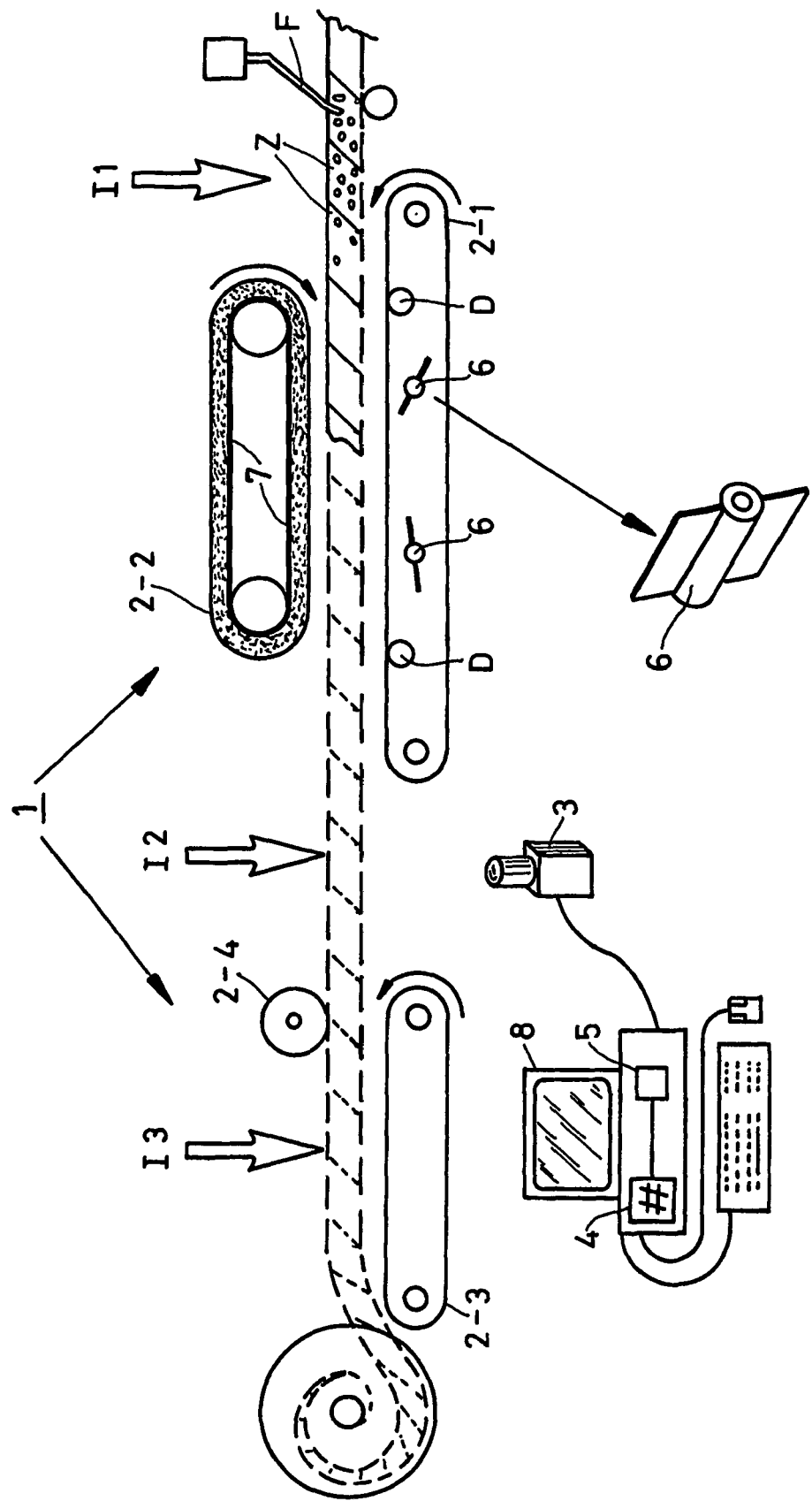

INSPECTION DEVICE FOR LOOSE OBJECTS, SUCH AS TABLETS

The invention relates to an inspection device for loose objects, for example tablets, comprising conveying means for conveying the objects to at least one inspection area.

The present invention also relates to a method by which loose objects are conveyed to at least one inspection area, and to packaged series of objects obtained therewith.

Such an inspection device and method are generally known. It is known in particular to subject objects that need to be inspected or verified to a form of (subsequent) inspection in order to reduce the occurrence of errors. For example, one or more persons inspect objects with regard to their number, possibly by means of an inspection device, usually if the objects are individualised in groups in compartments, trays or bags, and/or determine from external characteristics of the objects, such as the shape, the size or the colour thereof, whether the correct objects have been individualised. This method is used in particular upon verification of individualised groups of objects, such as tablets or pills, which have been individualised, whether or not in packaged condition, for each moment of ingestion by a patient. Tablets which have been (pre)packaged in bags by chemists or wholesale packagers are usually manually inspected in situ in that case, which is a labour-intensive and dull activity, which is moreover costly and which leads to many errors in practice, as a consequence of which patients receive too much or too little medication or the wrong medication, with all its consequences.

Also the known inspection devices, in which the objects are conveyed to an inspection area by conveying means, of necessity used in combination with the human factor, have appeared to be insufficiently reliable and insufficiently capable, if at all, of providing a solution for this problem.

The object of the present invention is to provide a more reliable inspection device and a corresponding method, in which the human factor is no longer a determining factor as regards the number of errors that occur during an inspection.

In order to a accomplish that objective, the inspection device according to the invention is characterized in that the inspection device also comprises mechanical impulse means for moving the objects apart prior to or during transport to said at least one inspection area.

Accordingly, the method according to the invention is characterized in that the objects are moved apart and subsequently are inspected in said at least one inspection area.

The advantage of the inspection device and the method according to the invention is that the mechanical impulse means enable a more adequate verification and inspection of individual objects after objects lying on top of each other, or against each other, to a greater or smaller extent have been moved apart and been spread over a larger area. Thus, a solid foundation is furthermore laid for automating the inspection method, in a manner yet to be explained in more detail, to a far-reaching extent whilst obtaining much more reliable inspection results. The inspection process can thus be carried out with less effort and with the use of fewer personnel whilst nevertheless achieving a better end result.

In principle, the objects may or may not be packaged in one embodiment of the inspection device according to the invention. In those cases in which the objects are not packaged yet, they will already have been individualised in groups in practice, so that the groups of objects only need to be packaged yet after inspection and approval. If, on the other hand, the groups are already packaged or pre-packaged, the reliability of the (pre)packaged final result can be inspected and enhanced by means of the inspection device according to the invention.

Another embodiment of the inspection device according to the invention is characterized in that the conveying means comprise first and second conveying elements, between which the objects are conveyed to the inspection area.

In this embodiment, the objects being conveyed to the inspection area are spread before arriving between the first and the second conveying elements, while being present between said elements and/or upon arrival in the inspection area. If objects of elongated section, for example, take up a more or less upright position, they will be laid flat between the two conveying elements, which has a positive effect as regards the recognition or identification thereof, which recognition or identification may form part of the inspection process.

A compact embodiment of the inspection device according to the invention is characterized in that the mechanical impulse means are incorporated in the first and/or the second conveying element.

A simplification of the inspection device according to the invention is characterized in that the mechanical impulse means comprise rotary means, which are preferably built up of one or more, possibly rotary, flaps which impart a mechanical impulse to the conveying means.

In practice, said rotary flaps beat against the conveying means with regularity. The resulting vibrations cause parts of the conveying means, on which the loose (so far) objects are present, to move the objects apart.

In another embodiment, in which the objects are not packaged yet or in which the objects are contained in a transparent package, the inspection device is furthermore characterized in that it comprises optical means being connected to the conveying means and being aimed at said at least one inspection area, which optical means function to record images of the objects in said at least one inspection area.

After said recording of images of the unpackaged objects or the objects contained in an at least partially transparent package, said images can be used for inspection and verification purposes.

Yet another embodiment of the inspection device according to the invention is characterized in that the inspection device comprises image recognition means connected to said optical means for inspecting the objects.

This makes it possible to use image recognition for realising an automated inspection process.

If means are provided for keeping image data and/or verification data obtained from the optical means up to date for a group of objects, a simple administration and possibly subsequent evaluation of said data will be possible, so that errors, in particular errors relating to medication, can easily be traced.

An embodiment which makes it possible to carry out a larger number of inspections by means of the inspection device is characterized in that the objects are contained in a package configured as a series of individual, interconnected packages, in which respective groups of objects are present. Such a series of packages, such as bags, is preferably present on a roll which takes-up little volume.

The present invention and its further advantages will now be explained in more detail with reference to the appended drawing. The FIGURE of said drawing shows a schematic diagram of an inspection device according to the invention by way of explanation also of the method according to the invention.

The FIGURE shows an inspection or verification device 1 intended for analysing loose objects. Since the loose objects may lie on top of each other, on their sides or against each other in all or in part, errors can easily occur upon verification. The errors may occur in counting or identifying the objects, for example, and/or in recognising the shape and/or the colour and/or the size of the objects. Hereinafter, the objects will be referred to as tablets or pills for the sake of simplicity, for which a correct and quick inspection is important in connection with the administration of the correct medication at various moments of ingestion during a day, both as regards the correct number and as regards the correct type and kind of medicine. The objects do not necessarily have to be medicines, however, they may also be all kinds of loose objects, whether or not packaged or yet to be packaged, which are to be counted or identified.

The objects being introduced into the device on the right-hand side, seen in the FIGURE, by conveying means 2 have been divided into groups and individualised at an earlier stage. Said groups may be packaged, but this is not necessary. Each group of tablets is usually intended for one or more moments of ingestion by a particular patient in, for example, a hospital or a nursing home. The inspection device 1 inspects or is used for inspecting the groups of tablets. If the groups of tablets are to be packaged, an inspection may also be carried out prior to said packaging, followed by an inspection after said packaging, if desired. To that end, a packaging machine (not shown) may be present on the left-hand side of the inspection device 1. Hereinafter it will be assumed for the sake of simplicity that packaged tablets are concerned. Such groups of tablets are preferably contained in a series of interconnected packages or bags Z, which are usually provided in the form of compact roll, which may or may not be wound on a reel. A bag Z from the roll is supplied to the conveying means 2 on the right-hand side in the FIGURE. During that stage, a first visual inspection may be carried out in a so-called inspection area I1 by personnel that is present. The bags Z will be transparent in that case. Said first visual inspection may be carried out with the aid of the optical means 3 aimed at one or more of the inspection area is I1, I2 and/or I3, as is shown only for the area I2, for the purpose of recording images—from above and/or from below—of the objects and/or groups of objects, if required. Backlighting may be used in that case, so that images rich in contrast will be obtained. In that case the bags Z will at least partially transmit electromagnetic waves having a frequency that lies within the operative frequency range of the optical means 3. The images may be stored in a memory 4 for subsequent evaluation or verification. The inspection device 1 may also comprise image recognition means 5 connected to the optical means 3 so as to enable an automatic inspection of the objects without any personnel being involved. The software that is required in order to realise this is known per se or it can be adapted to the expected recognition characteristics of the objects in question in a simple manner.

The inspection device 1 furthermore comprises mechanical impulse means 6 for moving the objects apart prior to and/or during their transport to the inspection area. This leads to an improved reliability of the detection and inspection of the objects or groups of objects, irrespective of the fact whether the inspection and/or image recognition is (are) carried out by personnel or automatically.

The conveying means 2 preferably comprise first and second conveying elements 2-1 and 2-2, respectively. The packaged series of objects coming from the roll are moved or pulled in the direction indicated by the arrows by means of one or more driven conveying elements 2-1 . . . 2-4. The mechanical impulse means 6 may be incorporated in the first conveying elements 2-1 at several different locations, if desired, in which case they will generally comprise a rotary means, such as rotary, generally more or less flexible flaps, which impart a mechanical impulse to the conveying means 2 upon rotation, causing the objects to move apart prior to or during transport by the conveying elements 2-1. A number of rigid flaps F may be fitted near the location where the bags Z are introduced into the device on the right-hand side of the device 1, which flaps cause upright objects to be laid flat.

In the illustrated double construction, the second conveying element 2-2 is positioned above the first conveying element 2-1. The second element 2-2, too, may be a driven element, and it is preferably driven at the same speed as the first element 2-1, in which case the tablets will not exhibit any tendency to rotate. The conveying elements 2-1, 2-2 may be driven continuously or intermittently. If the second conveying element 2-2, for example, is provided with a flexible layer 7 of foam rubber, for example, one or more objects clamped between the first and the second conveying elements 2-1 and 2-2 will indeed be laid flat, but since there is no difference in the speed at which the elements 2-1 and 2-2 move, objects lying flat on the conveying element will not be pushed into an oblique or upright position. The layer 7 of elastic material will not damage the objects. Moreover, the vibrating and shaking of the conveying element 2-1 and/or 2-2 imparted by the mechanical impulse means 6 can be adjusted to take place with such an intensity and period time or rotational speed that the objects will move apart during transport between the elements 2-1 and 2-2. One possible embodiment of the device 1 may comprise damping means D, for example in the form of damping rollers D (as shown in the FIGURE), whose height and/or mutual spacing is adjustable, which damping means function to influence the movement of the tablets in the area in which the impulse means 6 are operative. Thus, the intensity of the impulse transmitted to the tablets is controlled via the damping means D, which are mounted on either side of the impulse means 6, as is shown in the FIGURE.

After leaving the zone between the elements 2-1 and 2-2, the series of objects move into the inspection area I2, where an image (which may be a second image) of the object is recorded. The objects will no longer lie on top of each other or against each other in this area, so that inspection and verification can take place in a simple and, if desired, automated manner, as already explained above.

The package may be provided with information relating the contents thereof, such as a code, for example a bar code, from which the number of objects and/or further data relating to the objects can be derived upon reading of the code. A bar code reader may be used for that purpose, which bar code reader may be incorporated in the optical means 3. The inspection device 1 furthermore comprises means 8, usually a (micro)processor or a PC having a sufficient large memory 4, for storing image and/or verification data of a group of objects and keeping said data up to date. Said verification data include, for example, the detected number of objects and/or the shape and/or the colour and/or the size of said objects. The detected number is compared with the number that has been read from the bar code. If the numbers do not correspond, the packaging in question is provided with a mark, i.e. possibly a warning, by means of a well-known printing device (not shown).

The FIGURE furthermore schematically shows the possibility to install a third conveying element 2-3, in which case images are recorded by the optical means 3 when the series of bags containing the objects pass from element 2-1 to element 2-3 and/or when they are present within the inspection area I3.

If a camera 3 is present in more than one inspection area, for example in order to obtain an even more precise identification and inspection of the bags and their contents, several images of one and the same bag will be made, and the data obtained therefrom can be combined advantageously so as to achieve an even more reliable end result.

The invention claimed is:

1. An inspection device for objects, the inspection device comprising:
   means for conveying the objects to at least one inspection area, the means for conveying including,
      a driven first conveying unit configured to convey the objects, and
      a driven second conveying unit configured to convey the objects and to be driven at a same speed as the first conveying unit, the objects being packaged tablets contained in a series of interconnected packages, the objects being conveyed at the same speed to the at least one inspection area by the first conveying unit and the second conveying unit, while being clamped, to lay the objects flat, between the first conveying unit and the second conveying unit; and
   means for imparting a mechanical impulse for moving the objects apart prior to or during a transport of the objects to the at least one inspection area by the first conveying unit and the second conveying unit.

2. The inspection device according to claim 1, wherein the means for imparting is incorporated in at least one of the first conveying unit or the second conveying unit.

3. The inspection device according to claim 1, wherein the means for imparting comprises means for rotating a flap that imparts the mechanical impulse.

4. The inspection device according to claim 1, wherein the means for imparting includes one or more flaps, which impart the mechanical impulse to the means for conveying.

5. The inspection device according to claim 1, wherein the series of interconnected packages are at least partially transparent.

6. The inspection device according to claim 5, further comprising:
   means for recording images of the objects in the at least one inspection area, the means for recording being connected to the means for conveying and being aimed at the at least one inspection area.

7. The inspection device according to claim 6, further comprising:
   means for inspecting the objects, the means for inspecting being connected to the means for recording.

8. The inspection device according to claim 6, further comprising:
   means for storing and for keeping at least one of image data and verification data obtained from the means for recording up to date for a group of the objects.

9. The inspection device according to claim 1, wherein, in individual packages of the series of interconnected packages, respective groups of tablets are present.

10. The inspection device according to claim 9, wherein the series of interconnected packages are present on a roll.

11. The inspection device according to claim 1, wherein the first conveying unit and the second conveying unit pull the objects to the at least one inspection area.

12. The inspection device according to claim 1, further comprising:
   a camera that records images of the objects in the at least one inspection area and reads a code from an at least partially transparent package of the series of interconnected packages, the objects being contained in the at least partially transparent package, the camera connected to the means for conveying and aimed at the at least one inspection area;
   a processor that performs an image recognition of the images and compares a number of the objects detected by the camera to a number of the objects read from the code, the processor being connected to the camera; and
   a printing device that provides a mark on the at least partially transparent package, when the number of the objects detected by the camera does not correspond with the number of the objects read from the code.

13. The inspection device according to claim 1, wherein the second conveying unit includes a layer of foam rubber to clamp the objects to lay flat between the first conveying unit and the second conveying unit.

14. A method, comprising:
   conveying, with a driven first unit and a driven second unit, objects to at least one inspection area, the first unit and the second unit being driven at a same speed;
   imparting a mechanical impulse to move the objects apart prior to or during a transport of the objects to the at least one inspection area by the first unit and the second unit;
   clamping the objects, to lay the objects flat, between the first unit and the second unit, the objects being conveyed at the same speed to the at least one inspection area by the first unit and the second unit during the clamping; and
   inspecting the objects in the at least one inspection area, wherein the objects are packaged tablets contained in a series of interconnected packages.

15. The method according to claim 14, wherein, in the inspecting step, the objects are contained in a transparent, individualized package of the series of interconnected packages.

16. The method according to claim 14, wherein the inspecting step comprises performing an automated optical inspection in the at least one inspection area.

17. The method according to claim 14, wherein the inspecting step comprises performing a processor-controlled image recognition.

18. The method according to claim 14, wherein the inspecting step comprises counting the objects, and recognizing a shape of one of the objects, a color of one of the objects, or a size of one of the objects.

19. An inspection device for objects, the inspection device comprising:
   a conveying unit configured to convey the objects to at least one inspection area, the conveying unit including,
      a driven first conveying unit configured to convey the objects, and
      a driven second conveying unit configured to convey the objects and to be driven at a same speed as the first conveying unit, the objects being packaged tablets contained in a series of interconnected packages, the objects being conveyed at the same speed to the at least one inspection area by the first conveying unit and the second conveying unit, while being clamped, to lay the objects flat, between the first conveying unit and the second conveying unit; and
   a mechanical impulse unit that imparts a mechanical impulse to move the objects apart prior to or during a transport of the objects to the at least one inspection area by the first conveying unit and the second conveying unit.

* * * * *